(12) United States Patent
Silverman et al.

(10) Patent No.: US 7,467,560 B2
(45) Date of Patent: Dec. 23, 2008

(54) BROADBAND LONG PULSE ULTRASONIC INSPECTION

(75) Inventors: Eugene Ben Silverman, Ellicott City, MD (US); Richard Skallos, Severna Park, MD (US)

(73) Assignee: Berkeley Springs Instruments LLC, Great Cacapon, WV (US)

( * ) Notice: Subject to any disclaimer, the term of this patent is extended or adjusted under 35 U.S.C. 154(b) by 834 days.

(21) Appl. No.: 10/528,410

(22) PCT Filed: Sep. 24, 2003

(86) PCT No.: PCT/US03/29875

§ 371 (c)(1),
(2), (4) Date: Mar. 18, 2005

(87) PCT Pub. No.: WO2004/029564

PCT Pub. Date: Apr. 8, 2004

(65) Prior Publication Data

US 2006/0010995 A1 Jan. 19, 2006

(51) Int. Cl.
*G01M 19/00* (2006.01)
*G01H 1/00* (2006.01)
*G01N 29/00* (2006.01)

(52) U.S. Cl. .................. 73/865.8; 73/623

(58) Field of Classification Search .............. 73/866.5, 73/865.8, 623, 601, 620, 627–629; 702/39, 702/33–35
See application file for complete search history.

(56) References Cited

U.S. PATENT DOCUMENTS

| | | | | |
|---|---|---|---|---|
| 5,205,174 A | * | 4/1993 | Silverman et al. | 73/623 |
| 5,456,114 A | * | 10/1995 | Liu et al. | 73/597 |
| 5,627,800 A | * | 5/1997 | Kotler et al. | 367/127 |
| 6,104,970 A | * | 8/2000 | Schmidt et al. | 701/2 |
| 6,253,615 B1 | * | 7/2001 | Simmonds et al. | 73/579 |
| 7,017,432 B2 | * | 3/2006 | Silverman et al. | 73/865.8 |

* cited by examiner

*Primary Examiner*—Helen C. Kwok
(74) *Attorney, Agent, or Firm*—Steptoe & Johnson PLLC

(57) ABSTRACT

A robotic ultrasonic inspection vehicle is provided with one or more transducers which are driven by a long, broadband excitation pulse for insonifying a sample subject to inspection. The long, broadband excitation pulse can be chirped. The robotic vehicle also can include a drive circuit for coupling the excitation pulse to the transducer. Data associated with the excitation pulse is used to gate off the drive circuitry at an appropriate time. The robotic vehicle may traverse a combustion prone region and therefore electrical parameters may be limited to intrinsically safe levels. However electrical parameters may safely be converted to higher levels so long as the conversion is inhibited to occur only after the vehicle has left a combustion prone region and entered a region of minimal risk of combustion.

20 Claims, 4 Drawing Sheets

BROADBAND LONG PULSE ULTRASONIC INSPECTION

FIELD OF THE INVENTION

The invention relates to the ultrasonic inspection of materials, particularly walls of fluid reservoirs and the like.

BACKGROUND OF THE INVENTION

Traditional non-destructive testing of ferrous metals using ultrasound (UT) is typically accomplished with pulse sources that stimulate the plate under test.

The piezoelectric ultrasound transducer converts the pulse of electrical energy into an acoustic pressure wave (sound). The pressure wave is coupled the surface of the plate via the fluid in the reservoir, or by an equivalent acoustic coupler. Most of the energy (sound) is reflected from the front surface of the plate due to the acoustic impedance discontinuity. Some energy enters the plate travels through the plate and is reflected from the back surface of the plate back towards the front surface. Some of the reflected energy leaves the front of the plate and some is reflected towards the back surface of the plate. This reflection process continues. Energy is lost from the plate boundary surfaces for each reflection. Energy lost at the front of the plate travels back towards the ultrasound transducer where it is received and converted back to electrical energy. The electrical pulses received represent the two way acoustic front-to-back acoustic travel times. The thickness of the plate can be estimated by measuring the pulse to pulse travel time and knowing the velocity of sound in the plate under test. By searching for a reduction in the plate thickness, one can locate plate corrosion or pitting.

The industry has long been aware of the need to inspect the walls of fluid reservoirs, particularly when those walls are metal. In this application, the term "walls" refers to both bottom and side walls of a structure or tank. Special problems are engendered when the fluid maintained in the reservoir is combustible.

One solution to the problem is the technology described in Silverman U.S. Pat. No. 5,205,174. This patent describes a robotic vehicle which can travel into a partly filled fluid reservoir and traverse the tank for inspection. The '174 patent describes both optical and ultrasonic inspection technologies.

The pulse echo technique works well on pristine plate. High pulse amplitudes (250+ volts) are required to obtain reasonable signal to noise ratios when debris or rough surfaces (corrosion) are present on the plate. The transducer is typically stimulated or "pinged" with a narrow pulse with duration in the 100 nanosecond range. The mechanical properties of the ultrasound transducer control the transmitted acoustic pulse. The measurement time or thickness resolution is primarily controlled by the transducer's acoustic bandwidth. If the transducer rings for an extended period of time, this can mask small returns close to the front surface as would be seen from the front surface. Additionally, the front surface energy is typically large with respect to the desired wall reflections and is normally clipped in the receiving electronics.

A particular problem in tanks storing combustible fluids is that the inspection system must first travel through a region devoid of the fluid before traveling into the fluid containing region in order to reach the wall to be inspected. Traversing the fluid-free regions is a problem because when the reservoir stores combustible fluid, the fluid-free region typically contains combustible vapors.

Standards bodies have devised standards for instruments which work or travel through regions containing combustible vapors. Limitations on the voltage and current levels found on apparatus in the combustible region allows that apparatus to be considered "intrinsically safe".

On the other hand, limiting the inspection system to voltage and current levels which are below the thresholds established in these standards presents problems in conducting an effective inspection.

SUMMARY OF THE INVENTION

Thus the present invention is directed at improved ultrasonic inspection methodology for inspecting the walls of fluid reservoirs. The inspection system of the invention is capable of safely inspecting tanks storing combustible fluids.

An alternate way to interrogate material is to determine the transfer function by insonifying the material continuously with a range of frequencies across a specific bandwidth over a finite period of time. The bandwidth and pulse duration is determined by what best represents the degree of resolution necessary to determine the integrity of the material (such as material thickness, or the depth of a pit). The returned signal represents the system transfer function of the transmit electronics, transducer, liquid-to-material interface, the material itself and the receive electronics. A receive signal representing the transfer function of the transmit electronics, receive electronics and the transducer can be captured by using a very thick calibration block, or acoustic mirror. This calibration signal becomes a transmit replica that can be correlated with the receive signals from walls under test. The correlation provides received signal pulse compression to produce impulses which represent the front and rear surfaces of the wall under test.

In addition to correlation, the transmit replica signal can be adaptively subtracted from the receive signals under test removing the front surface signal, leaving only the wall thickness response. Further analysis can be conducted on the received waveforms to estimate the plate transfer function in order to identify other characteristics of importance (discontinuities, roughness corrosion, etc.).

Unique characteristics associated with the use of long pulse chirp signals for NDT applications within an in-service robotic operational environment include:

1. Combined use of a chirp signal with signal correlators to determine material transfer functions.
2. Chirp signals which produce meaningful results can be produced with significantly lower power than traditional pulse-echo signals which lends itself to use in environments that are potentially explosive.
3. The use of a chirp bandwidth of low frequency is less susceptible to the influences of sludge interference as compared to single, high frequency pulse-echo transducers.
4. A wider variety of transducer electromechanical characteristics can be applied to a wider range of materials in order to interrogate unique material features.
5. When combined with in-service robotic system used to examine the integrity of aboveground storage tank floors within highly volatile environments, signals can be made intrinsically safe.
6. The long pulse, even at low voltage, can provide as much or more transmit acoustic energy when compared to a short pulse system.
7. Control of the transmitted acoustic energy in time, amplitude and frequency (bandwidth) is enhanced by the available time duration for the pulse.

8. Time, amplitude and frequency control can provide maximum power transfer from the amplifier to the transducer across all frequencies if desired, i.e., the transmit signal can be designed to match the inverse of the transducer transfer function within system frequency limits.
9. Time, amplitude and frequency control can provide a limited bandwidth low frequency signal if desired for high sludge/debris situations.
10. Time, amplitude and frequency control can be utilized to generate simple linear frequency swept amplitude weighted signals (i.e., chirps) or complex waveforms, including pseudo random and high order components.

Accordingly, in one respect the invention provides an ultrasonic inspection system for inspecting walls of fluid reservoirs comprising a robotic vehicle;

a transducer supported on the robotic vehicle and responsive to electrical energy for emitting corresponding sonic energy in a chosen direction, a support for the transducer on the robotic vehicle positioning the transducer so the chosen direction is broadside to a selected wall of fluid reservoir, a drive circuit energizing the transducer with a broadband electrical pulse of duration in excess of that necessary for the sonic energy to transit the selected wall from one face to another, and an amplifier coupled to the transducer for receiving the signal from the transducer in response to sonic energy received from the selected wall.

In preferred embodiments the broadband electrical pulse includes energy up to about 8 MHz, for certain other applications, energy up to about 5 MHz may be used and in still other embodiments we may restrict energy to about 3.5 MHz or less.

More particularly, the ultrasonic inspection system includes an array of transducers, each transducer in the array supported to have chosen directions which are substantially parallel wherein the drive circuit energizes each transducer with the broadband electrical pulse of substantially identical duration but offset in time from one another and wherein the amplifier has a separate channel for each transducer in the array.

In a preferred embodiment each transducer is time multiplexed. One transducer transmits and receives for a period of time, then the next and so on. However, alternatively, each transducer could be stimulated with an unique pulse of different time, amplitude and frequency information.

The ultrasonic inspection system further includes control means for de-energizing the drive circuit predetermined time after initiation of the broadband electrical pulse.

In connection with another aspect, the inspection instrument includes a gated drive circuit, more particularly, a gated drive circuit which is gated off at the termination of the inspection pulse. In particular, the drive circuit for inspection system for ultrasonic inspection using a long broadband inspection pulse includes a receiver for receiving a long broadband inspection pulse, a gated amplifier coupled to said receiver with an output connected to an ultrasonic transducer for driving in the transducer with an amplified replica of said inspection pulse, and control means responsive to control data for controlling de-energization of the gated amplifier in response to said control data, whereby material under test adjacent to said transducer is subjected to ultrasonic energy produced by said transducer driven by said amplified inspection pulse.

In a particular aspect of the invention the gated amplifier includes an electronic amplifier coupled to an output of the receiver, a control switch, and a step-up converter coupled between the output of the controlled switch and the transducer.

In a further particular aspect of the invention the up converter comprises a transformer.

A further aspect of the invention relates to the extension of intrinsic safety. In this aspect electrical parameters for equipment within a combustion prone region are limited to levels at or below what is considered intrinsically safe. However, in order to efficiently conduct an inspection regime, allowance is made for electrical parameters to be increased beyond the intrinsically safe level but only for apparatus which is indicated to be outside the explosion prone region.

More particularly, the inspection apparatus includes a converter for increasing electrical energy parameters beyond an intrinsically safe level. The up converter, however, is only operated in response to an enabling signal. Production of the enabling signal requires an indication that at least some of the inspection apparatus is positively identified as being outside the explosion prone region. More particularly, an indication must be received that the inspection apparatus lies within a liquid environment.

This is implemented by maintaining one or more pressure switches on the inspection vehicle. In an initial phase of operation the inspection vehicle travels from outside the tank to be inspected, through the vapor region (which is combustion prone) and into the liquid environment. The converter which enables increase of electrical parameters beyond intrinsically safe levels is carried aboard the inspection vehicle. The inspection vehicle also includes a pressure switch which provides an indication (carried back to a control station via the umbilical) to indicate that the vehicle is within a liquid filled environment. Only when that control signal is received at the control location is a further control signal generated which, when received back at the inspection vehicle, will allow the up converter to be energized.

Thus in accordance with this aspect the invention comprises an inspection vehicle obtaining power from umbilical for operation in a liquid environment in the vicinity of a combustion prone region, the vehicle comprising:

a junction box coupled via said umbilical to a source of electrical energy having at least one electrical energy parameter within an intrinsically safe limit, a converter coupled to said junction box for increasing said at least one electrical energy parameter beyond said intrinsically safe limit, and a sensor for detecting the environment immediately surrounding said vehicle to allow operation of said converter only if said sensor indicates that said vehicle is within said liquid environment.

In accordance with a more specific aspect the sensor responds to pressure surrounding the inspection vehicle to allow operation of the converter only if the sensor detects pressure surrounding the inspecting vehicle indicating that the vehicle is submerged in said liquid environment.

In an even more specific aspect the invention provides an inspection system including the inspection vehicle as aforesaid and a power and signal source driving the umbilical, the inspection vehicle including:

a logic device for generating first and second control signals in response to a permissive signal from said power and signal source, a power and signal source including:

a first switch power source responsive to signals from said sensor allowing application of power to said vehicle via an umbilical, and a signal source responsive response to said sensor for generating said permissive signal in the event said sensor indicates that the vehicle is within said liquid environment.

In other respects the invention describes improvements in ultrasonic inspection for materials in the form used as the walls of fluid reservoirs. More particularly, the walls of fluid reservoirs are typically of metal, which have a thickness which is substantially smaller than any other dimensions of the walls.

BRIEF DESCRIPTION OF THE DRAWINGS

The invention will be further described in the following portion of the specification when taken in conjunction with the attached drawings in which like reference characters identify identical apparatus and in which.

DETAILED DESCRIPTION OF THE DRAWINGS

Figure 1:
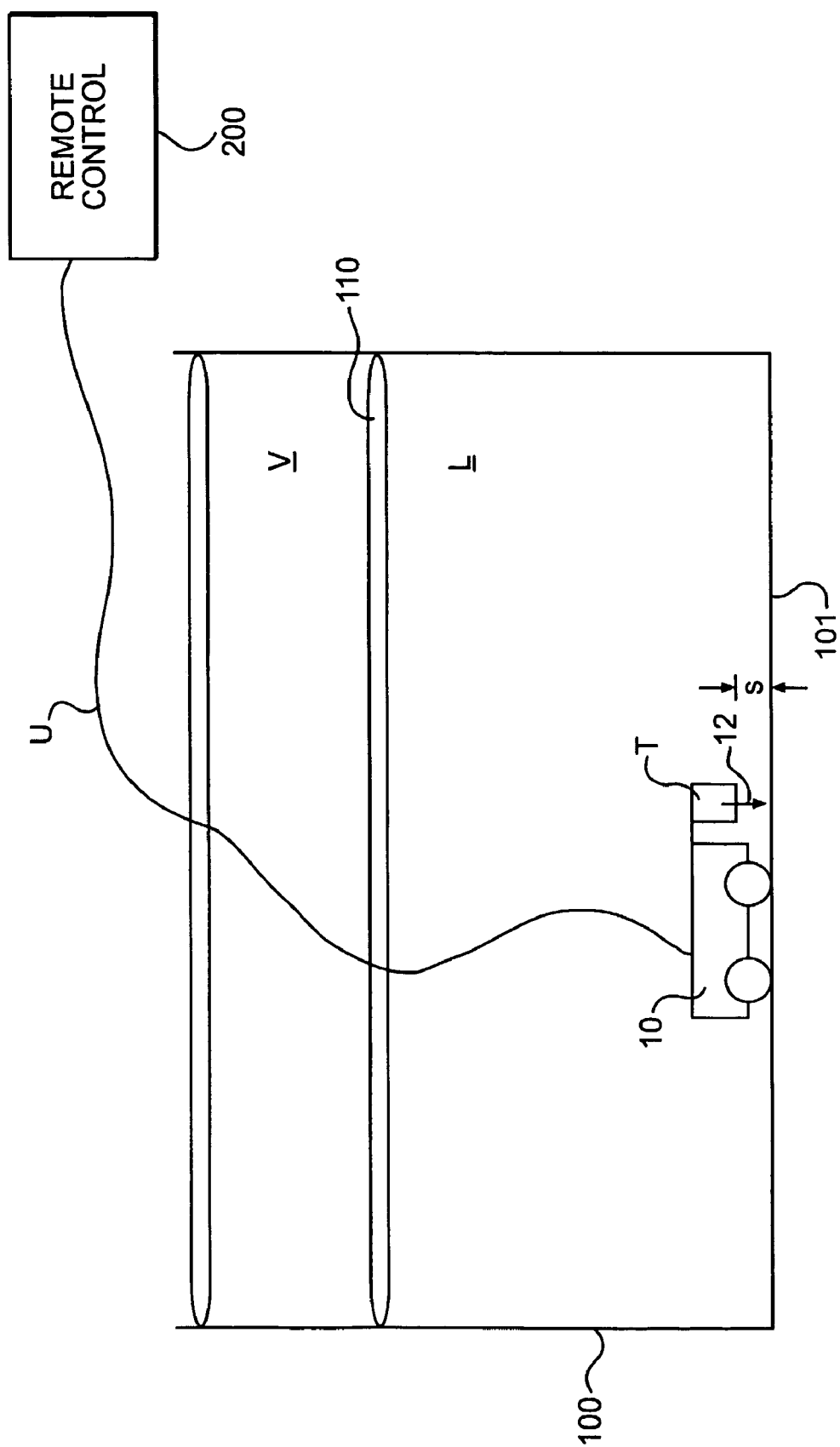
FIG. 1 is a schematic illustrating the robotic vehicle which carries the inspection system of the invention in a typical operating environment.

As indicated, FIG. 1 illustrates the typical environment within which the ultrasonic inspection system of the invention operates.

As shown in FIG. 1, a fluid reservoir 100 is partially filled with fluid having an upper surface 110. The upper surface of the fluid 110 then separates the reservoir 100 into a liquid-filled region L and a vapor-filled region V. A robotic vehicle 10 is located within the tank 100 adjacent to the bottom wall 101. The robotic vehicle 10 is powered so that it can navigate about the tank 100. Typically the robotic vehicle 10 is remotely controlled such as from the remote control location 200. Control signals and power (electric, hydraulic, etc.) are conveyed from a remote location 200 to the robotic vehicle 10 via the umbilical U. The umbilical U also carries signals from the robotic vehicle 10 back to the control location 200.

In typical use the robotic vehicle 10 is introduced into the reservoir 100 adjacent to its upper surface and navigates through the vapor region V and into the liquid region L prior to initiating an examination of the wall of the reservoir, such as the wall 100. The robotic vehicle 10 may be remotely controlled from the remote control 200. The robotic vehicle 10 includes circuitry, power conditioning electronics and the like. Visible from its exterior shape is, the transducer array T. The array T is supported so that each of the transducers (T1, T2, etc.) in the array T may launch sonic energy toward the wall 100 in the direction of the arrow 12. When the sonic energy impinges on the wall 101 it will be reflected by each of the discontinuities in the wall including at least the front face (closest to the vehicle 10 in the direction of the arrow 12) and the rear face (the face further from the vehicle 10 in the direction of the arrow 12) as well as any defects or discontinuities between the front face and the rear face. The reflected energy is converted by the transducers in the transducer array T from sonic to electrical energy to create a return signal or signature. This return signal is the result of the inspection process. The return signal can be further analyzed using correlation to discern particular features of the wall region that was inspected. The sonic energy emitted from the transducer array T is generated in response to a long, broadband inspection pulse conveyed from the remote control 200 to the vehicle via the umbilical U at the appropriate time. As will be described the inspection pulse is distributed to each of the transducers in a time offset manner. When enabled an up converter, provided for each of the transducers, increases at least one parameter of the pulse so as to more efficiently carry out an inspection. The transducers may be obtained from Krautkramer or Panametrics. At the termination of each inspection pulse at each transducer the drive circuit is cut off by the removal of a gating signal so as to prevent noise generated in the amplifier from corrupting the returned signal.

Figure 2:
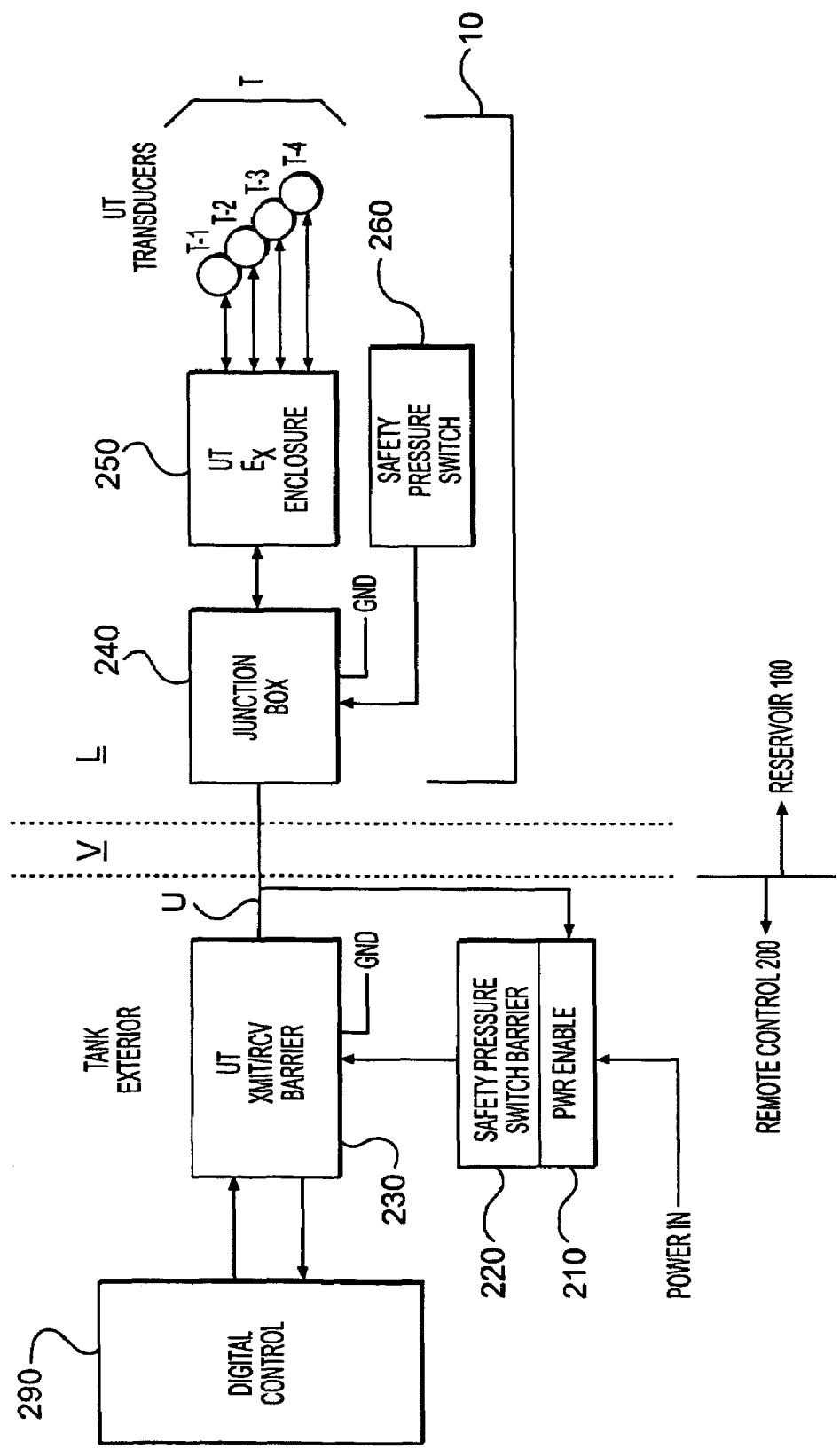
FIG. 2 is a block diagram of the inspection system and the location of the various components during normal operation.

FIG. 2 is a block diagram illustrating the functional relationship between the apparatus in the remote control unit 200 and important components of the robotic vehicle 10, particularly the components directed at the ultrasonic inspection system. In respect of motive power and control of the path of travel of the robotic vehicle 10 reference is made to the Silverman U.S. Pat. No. 5,205,174.

As shown in FIG. 2, the remote control unit 200 includes components driving the electrical signal carrying conductor components of the umbilical U. The umbilical U couples the remote control 200 to the robotic vehicle 10 traversing from the exterior of the tank through the vapor region V into the liquid region L.

The umbilical U carries electrical energy to power the ultrasonic inspection components of the robotic vehicle 10, it carries an electrical representation of the return signal from the transducers back to the remote control 200 for processing and it carries additional control and safety signals both from the remote control 200 to the vehicle 10 and from the vehicle 10 to the remote control unit 200.

As will be described, the digital control 290 provides signals to the transmit barrier 230 which are passed along to the inspection system to drive the ultrasonic inspection apparatus. In addition, the return signal is received at the barrier 230 and passed along to the digital control 290 for later analysis.

As shown in FIG. 2 at the remote control unit 200, power is applied to a power enable gate 210. The safety pressure switch barrier 220 allows power to be applied when appropriate, as will be explained.

Power and control signals flow from the safety pressure switch barrier 220 to the transmit receive barrier 230.

The robotic vehicle 10 includes, in connection with the inspection system, a junction box 240, an explosion proof enclosure 250, a safety pressure switch 260 and the ultrasonic transducer array T. As is shown in FIG. 2, the transducer array T is made up of a number of individual transducers. In the embodiment shown in FIG. 2 four transducers T1-T4 comprise the transducer array T. It should be apparent that the number of transducers in the array can be varied within wide limits including using a single transducer to using more than four transducers in the array. As is suggested by the illustration of FIG. 2, the longitudinal axis of the ultrasonic transducers in the array T are staggered in the direction of travel of the vehicle 10 so that by sequentially energizing different ones of the transducers in the array T, a swath of the path traveled by the robotic vehicle 10 can be inspected.

As has been mentioned, the voltage and current levels on the umbilical U are maintained below intrinsically safe levels as mandated by standards. It is an advantage of the invention that these electrical parameters can be increased at the robotic vehicle 10 for efficient generation of ultrasonic inspection energy. To maintain an intrinsically safe system, there should be no increase in the current or voltage parameters on any portion of the system which is in or adjacent to the combustion prone region V. To this end, an explosion-proof enclosure 250 is provided on the vehicle 10 within which current and/or voltage parameters may be increased without compromising intrinsic safety. The ability to increase voltage and/or current is limited to times during which the vehicle 10 is outside the vapor region V, for example, when vehicle 10 is within the liquid environment L and not within the vapor environment V. This condition is detected by the pressure switch 260. More particularly, the pressure switch is arranged to provide an indication that it is safe to allow increases in voltage and/or current levels within the explosion-proof enclosure 250. This safe indicator is postponed until the vehicle 10 is sufficiently within the liquid environment L so that the risk of combustion is minimal. For example, the pressure switch can be arranged to produce an indication of safety when the vehicle is three feet or more below the surface 110 of the liquid region L. As will be described, the safety indication generated by the safety pressure switch 260 is transmitted back via the junction box 240 and the umbilical U to the power enable element 210 of the safety pressure switch barrier 220. This condition generates a control signal which will be used by the transmit receive barrier 230 in a manner to be described. In one embodiment, electrical parameters in the system both in the umbilical U as well as in the vehicle 10 are normally limited to intrinsically safe levels. Only within the enclosure 250 is it possible to increase electrical parameters above intrinsically safe levels. However, a control signal from the power enable 210 is required to be received at the enclosure 250. This control signal is not generated until the pressure switch 260 indicates that the vehicle is safely within the liquid environment L.

Figure 3:
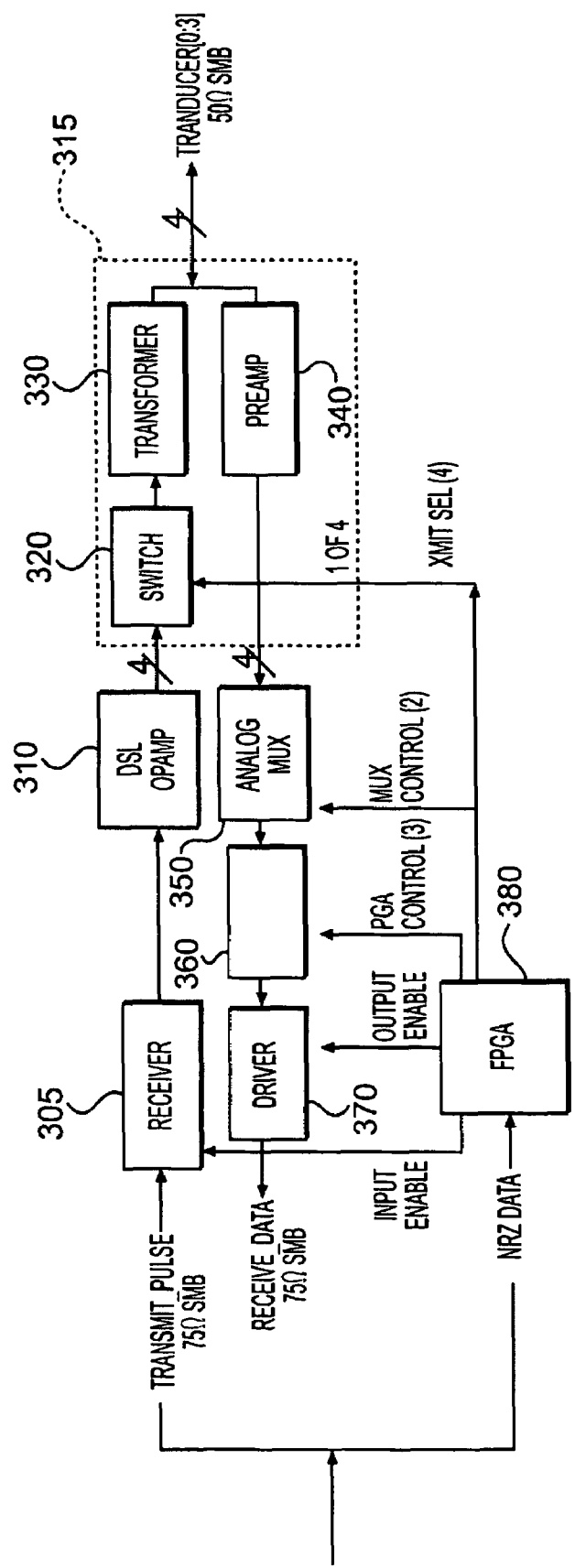
FIG. 3 is a block diagram of the inspection system itself.

FIG. 3 shows a block diagram of the components generating a drive signal for the transducers of the transducer array T. The equipment shown in FIG. 3 is maintained within the explosion-proof enclosure 250.

Referring now to FIG. 3, the drive circuit for the transducers in the array T includes a receiver 305 which is driven by the transmit pulse output of the junction box 240 from the umbilical U. The receiver 305 also receives an input enable control signal from the gate array 380. The output of the receiver is fed through amplifier 310 to the per transducer circuitry 315. Circuitry 315 includes a switch 320, an up converter 330 and a preamplifier 340 for each of the transducers in the array T. The switch 320 also receives a selection control signal from the gate array 380. When enabled, the switch 320 provides an output to the up converter 330 which in a preferred embodiment is a transformer. The output of the transformer 330 is coupled to the associated transducer in the transducer array. The transducer output (i.e., the return signal) is coupled in turn to a preamplifier 340 which is connected to a multiplexer 350. The multiplexer 350 also receives a control signal from the gate array 380. The output of multiplexer 350 is applied to the programmable amplifier 360 which also receives an enable signal from the gate array 380. The output of the PGA 360 is coupled to a driver 370 which also receives an output enable signal from the gate array 380. Finally, the output of the driver is coupled through the junction box 240 back unto the umbilical U and thereby connected back to the transmitter receive barrier 230 for further processing.

The programmable gate array 380 implements two programmable functions. As has been indicated there are a number of transducers in the array T. In addition, there is a per-transducer circuit 315 for each transducer in the array. The programmable gate array 380 staggers the energization and deenergization of each of the transducers by sequentially enabling and then disabling the transducers in turn. The order in which the transducers are enabled and the duration of the enablement and the time at which they are disabled is controlled by the gate array 380 in response to data received from the remote location, as will be described. At this point it is worthwhile noting that the gate array 380 provides a transmit select signal for each switch 320. The transmit select signal goes active, enabling the switch 320 when the corresponding channel is to be enabled. Likewise, the transmit select signal goes low to disable the switch 320 at the termination of the transducer energization.

A second function for the programmable gate array is gain control for the programmable amplifier 360. In this fashion the output level of the return signal can be adjusted, on the fly, by adjusting the control signal to vary the programmable gain of the amplifier 360.

Finally, a third function is to enable the receiver 305. As has been noted, the array of signals is generated by the gate array 380 in response to data received from the remote location 200 via the umbilical U. The various enabling and select signals are produced only when the rewrite control 200 has received a safe indication from the pressure switch.

The drive signal which is received at the explosion-proof enclosure 250 during typical operation has two components, received in time sequence. The first component (not illustrated) contains a multi-element control signal. This control signal comprises (in a preferred embodiment) NRZ data to program the gate array 380. This data produces the control signals which are required to enable and disable various components shown in FIG. 3.

Figure 4:
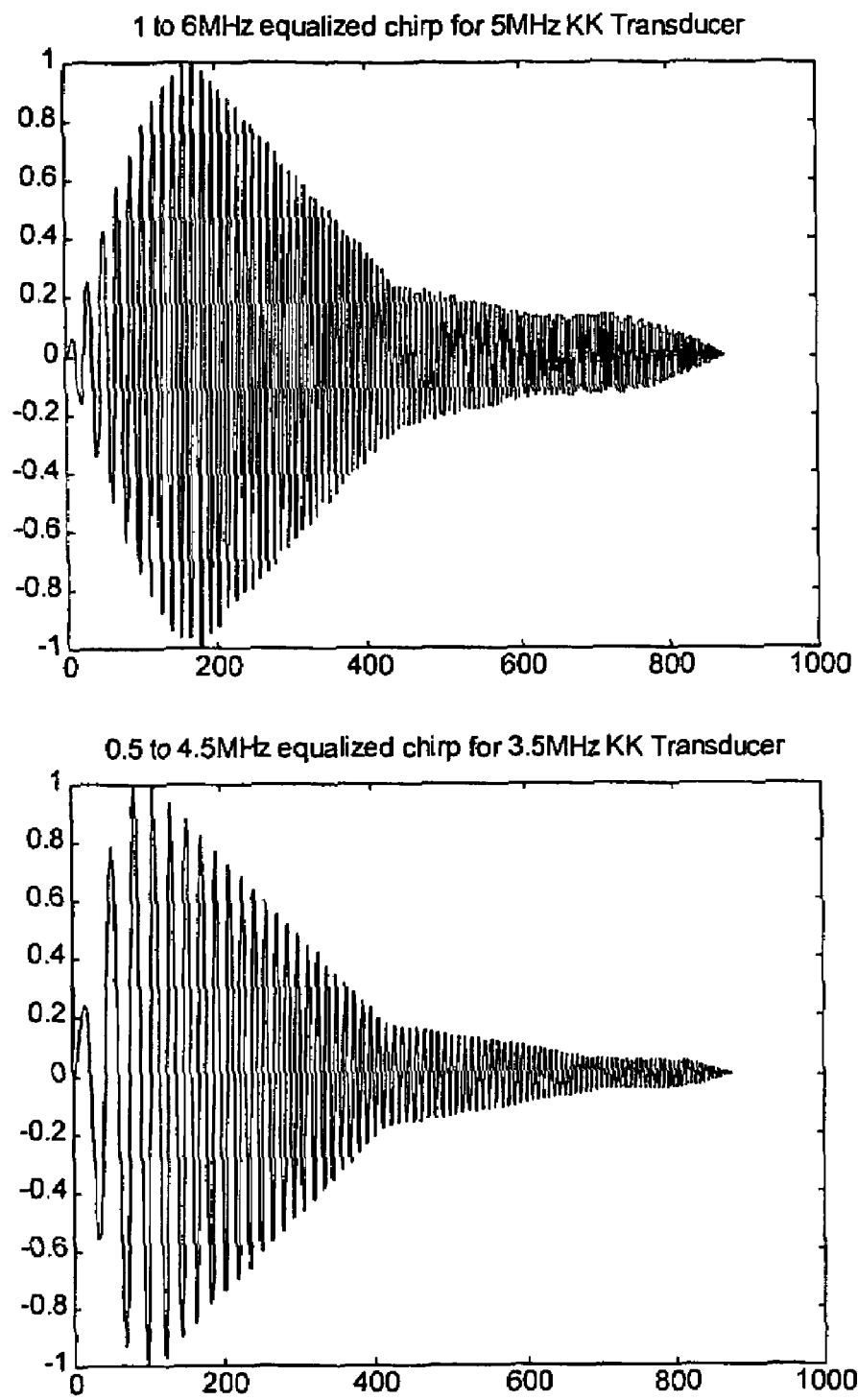
FIG. 4 illustrates a typical wave form used to drive the portion of the inspection system carried aboard the robotic vehicle.

FIG. 4 illustrates two different examples of the second component, i.e., a broadband long excitation pulse which is used to create the sonic pulse for inspection of the tank walls. One of the two waveforms illustrated in FIG. 4 is a 1 to 6 MHz equalized chirp for 5 MHz KK transducer and the other waveform is a 0.5 to 4.5 MHz equalized chirp for a 3.5 MHz KK transducer. Both the pulses illustrated in FIG. 4 are 35 microseconds in duration. Either of the inspection pulses of FIG. 4 has two important characteristics in a preferred embodiment.

In the first place it is referred to as a "long" pulse. This means that the duration of the pulse is long relative to the time expended by the sonic energy traversing the material to be inspected. For example, the velocity of sonic energy in steel is about 0.233 inches/microsecond. Two way travel time for steel=2×1 inch/0.233 inch/usec=8.58 microseconds per inch. Where wall thickness is ¼ inch, the pulse of 35 microseconds is "long" relative to the transit time for that wall which would be about 2.1 microseconds. There is another practical limitation on the pulse duration which is imposed by the geometry, i.e. the pulse travels from the transducer to the material to be inspected and then back. Ideally the duration of the pulse should be shorter than the delay in transiting twice the gap between transducer and inspection material. This insures that the tail end of the pulse has been launched before the reflection reaches the transducer. The two way travel time for an oil path (a reasonable estimate for the environment of the example described here) is about 37 microseconds per inch. With a gap of 1-3" we meet this requirement (35 microseconds is shorter than the delay for 1" and so is clearly shorter than the delay for longer gaps).

Another characteristic of the pulse is that it is broadband, e.g., the bandwidth in a preferred embodiments is 3.5 MHz or 5 MHz. In general, the higher the bandwidth, the better is the resolution for measuring thickness; this is how we can determine the presence of pits and other non-uniformities. We prefer to use as much bandwidth as possible to increase the thickness resolution. On the other hand, when working in environments which include sludge and high corrosion, there is an impetus to keep the frequency low in order to reduce the effects of sludge and surface roughness. Thus in a preferred embodiment, the bandwidth is preferably 3.5 MHz. Moreover, in a preferred embodiment, the input pulse is frequency swept so that it might be referred to as a chirp signal. The pulse of FIG. 4 may be a 3.5 MHZ chirp with components from 0.5 to 4.5 MHz, an equalization slope to approximate the inverse of the transducer response with 10% cosine weighting.

It should be apparent that while an example of the invention has been disclosed herein, various changes can be made to the exemplary details described herein without departing from the spirit and scope of the invention. Accordingly the invention should not be limited by the particular parameters described in the foregoing specification but should be interpreted in accordance with the claims appended hereto.

We claim:

1. An ultrasonic inspection system for inspecting walls of fluid reservoirs comprising
   a robotic vehicle,
   a transducer supported on the robotic vehicle and responsive to electrical energy for emitting corresponding sonic energy in a chosen direction,
   a support for the transducer on the robotic vehicle positioning the transducer so the chosen direction is broadside to a selected wall of the fluid reservoir,
   a drive circuit energizing the transducer with a broadband electrical pulse of duration in excess of that necessary for the sonic energy to transit the selected wall from one face to another, and
   an amplifier coupled to the transducer for receiving a signal from the transducer in response to sonic energy received from the selected wall.

2. The inspection system of claim 1 wherein the broadband electrical pulse includes energy up to about 3.5 MHz.

3. The inspection system of claim 1 wherein the broadband electrical pulse includes energy up to about 5 MHz.

4. The ultrasonic inspection system of claim 1 which includes an array of transducers, each transducer in the array supported to have chosen directions which are substantially parallel, wherein the drive circuit energizes each transducer with the broadband electrical pulse of substantially identical duration but offset in time from one another and wherein the amplifier has a separate channel for each transducer in the array.

5. The ultrasonic inspection system of claim I which further includes control means for de-energizing said drive circuit at a predetermined time after initiation of the broadband electrical pulse.

6. The ultrasonic inspection system of claim 5 wherein the control means includes a gate array responsive to control data received just prior to a rise of said broadband electrical pulse.

7. The ultrasonic inspection system of claim 1 wherein the broadband electrical pulse is swept in frequency.

8. A drive circuit for an inspection instrument for ultrasonic inspection using a long broadband inspection pulse, comprising:
   a receiver for receiving a long broadband inspection pulse,
   a gated amplifier coupled to said receiver with an output connected to an ultrasonic transducer for driving said transducer with an amplified replica of said inspection pulse, and control means responsive to control data for controlling deenergization of said gated amplifier in response to said control data, whereby material under test adjacent to said transducer is subjected to ultrasonic energy produced by said transducer driven by said amplified inspection pulse.

9. A drive circuit as recited in claim 8 wherein said gated amplifier includes:
   an electronic amplifier coupled to an output of said receiver,
   a controlled switch, and
   a step up converter coupled between an output of said controlled switch and said transducer.

10. A drive circuit as recited in claim 9 wherein said step up converter comprises a transformer.

11. A drive circuit as recited in claim 8 wherein said control means comprises a gate array, wherein said gated amplifier includes a controlled switch controlled by an output of said gate array.

12. A drive circuit as recited in claim 8 wherein said transducer has a bandwidth in a range of about 3.5 MHz to 5 MHz.

13. An inspection vehicle obtaining power from an umbilical for operation in a liquid environment in the vicinity of a combustion prone region, said vehicle comprising:
   a junction box coupled via said umbilical to a source of electrical energy having at least one electrical energy parameter within an intrinsically safe limit,
   a converter coupled to said junction box for increasing said at least one electrical energy parameter beyond said intrinsically safe limit, and
   a sensor for detecting the environment immediately surrounding said vehicle to allow operation of said converter only if said sensor indicates that said vehicle is within said liquid environment.

14. The inspection vehicle of claim 13 wherein said umbilical provides electrical energy with voltage and current of levels which are intrinsically safe for the combustion prone region.

15. The inspection vehicle of claims 13 wherein said sensor responds to pressure surrounding said inspection vehicle to allow operation of said converter only if said sensor detects pressure surrounding said inspetion vehicle indicating that said vehicle is submerged in said liquid environment and not in said combustion prone region.

16. An inspection system including the inspection vehicle of claim 15 and a power and signal source driving said umbilical, said inspection vehicle including:
   a logic device for generating first and second control signals in response to a permissive signal from said power and signal source,
   said power and signal source including:
   a first switched power source responsive to signals from said sensor for allowing application of power to said vehicle via said umbilical, and
   a signal source responsive to said sensor for generating said permissive signal in the event said sensor indicates that the vehicle is within said liquid environment.

17. The inspection system of claim 16 wherein the first and second control signals are coupled to said converter allowing said increase in said electrical energy parameter.

18. The inspection system of claim 17 wherein said converter includes at least one transformer enabled by one of said control signals.

19. The inspection vehicle of claim 13 wherein the converter is contained in an explosion proof container.

20. The inspection system of claim 16 wherein the converter is contained in an explosion proof container.

* * * * *